US008017314B2

(12) United States Patent
Abel et al.

(10) Patent No.: US 8,017,314 B2
(45) Date of Patent: Sep. 13, 2011

(54) IMMERSION SENSOR FOR MEASURING THE CONCENTRATION OF AN ANALYTE WITH THE HELP OF AN OXIDASE

(75) Inventors: Peter Abel, Zinnowitz (DE); Rudolf Ehwald, Berlin (DE); Uwe Beyer, Bern (SE)

(73) Assignee: Roche Diagnostics International AG, Steinhausen (CH)

( * ) Notice: Subject to any disclaimer, the term of this patent is extended or adjusted under 35 U.S.C. 154(b) by 539 days.

(21) Appl. No.: 12/032,456

(22) Filed: Feb. 15, 2008

(65) Prior Publication Data

US 2008/0182286 A1    Jul. 31, 2008

Related U.S. Application Data

(60) Division of application No. 10/687,529, filed on Oct. 16, 2003, now Pat. No. 7,335,286, which is a continuation of application No. PCT/CH02/00209, filed on Apr. 15, 2002.

(30) Foreign Application Priority Data

Apr. 18, 2001  (DE) .................................. 101 19 036

(51) Int. Cl.
*C12Q 1/00*          (2006.01)
*C12Q 1/26*          (2006.01)
(52) U.S. Cl. ................ 435/4; 435/25; 600/347
(58) Field of Classification Search ............... 435/4, 14, 435/25, 174, 287.1, 287.5; 204/403.01, 403.06, 204/403.09, 403.1, 403.11, 403.14; 600/347
See application file for complete search history.

(56) References Cited

U.S. PATENT DOCUMENTS

| | | | |
|---|---|---|---|
| 4,680,268 A | | 7/1987 | Clark, Jr. |
| 4,750,496 A | | 6/1988 | Reinhart et al. |
| 5,130,231 A | * | 7/1992 | Kennedy et al. ................ 435/4 |
| 5,200,051 A | * | 4/1993 | Cozzette et al. ......... 204/403.07 |
| 5,250,419 A | * | 10/1993 | Bernard et al. ............... 600/348 |
| 5,428,123 A | | 6/1995 | Ward et al. |
| 5,589,133 A | * | 12/1996 | Suzuki ........................... 422/79 |
| 6,001,067 A | | 12/1999 | Shults et al. |
| 6,030,827 A | * | 2/2000 | Davis et al. ................. 435/287.1 |
| 7,335,286 B2 | | 2/2008 | Abel et al. |
| 2003/0036052 A1 | * | 2/2003 | Delwiche et al. ................ 435/4 |

FOREIGN PATENT DOCUMENTS

| | | |
|---|---|---|
| DE | 195 07 107 | 8/1996 |
| DE | 195 47 923 | 11/1999 |
| EP | 535898 A1 * | 4/1993 |
| EP | 539625 | 5/1993 |
| WO | WO 96/14026 | 5/1996 |
| WO | WO 97/15827 | 5/1997 |

OTHER PUBLICATIONS

Von Woedtke, T., et al. "Subpicosecond-pulse laser microstructuring for enhanced reproducibility of biosensors." Sensor and Actuators, B. 1997. B42(3): 151-156.
U. Fischer, et al. "Clinical Usefulness of the Glucose concentration in the Subcutaneous Tissue-Properties and Pitfalls of Electrochemical Biosensors", Norm. Metab. Res. 26 (1994) pp. 515-522.
G.P. Rigby, et al., "In Vivo glucose monitoring with open microflow—influences of fluid composition and preliminary evaluation in man", Analytica Chimica Acta 385 (1999) pp. 23-32.
V. Thome-Duret, et al. "Modification of the Sensitivity of Glucose Sensor Implanted into Subcutaneous Tissue", Diabetes & Metabolism (Paris) 22 (/3), (1996) pp. 174-178.
"The Effect of Intensive Treatment of Diabetes on the Development and Progression of Long-Term Complications in Insulin-dependent Diabetes Mellitus", The New England Journal of Medicine, vol. 329, No. 14 (Sep. 30, 1993), pp. 977-986.
Dilber S. Bindra, et al., "Design and in Vitro Studies of a Needle-Type Glucose Sensor for Subcutaneous Monitoring", Anal. Chem. 63 (1991) pp. 1692-1696.
H. Schneider et al, "Mass Transfer Characterization of a New Polysulfone Membrane", Artificial Organs, 9(2); 180-183, Raven Press, New York; 1995 International Society for Artificial Organs.
Zick, R., Schiewitz, J. "Glukosensor. Erste Klinische Erfahrungen", Diabetes Aktuell 4 (2000).
Gough et al. Anal. Chem. 57, 2351-2357 (1985).

* cited by examiner

*Primary Examiner* — Allison M. Ford
*Assistant Examiner* — Susan E. Fernandez
(74) *Attorney, Agent, or Firm* — Dinsmore & Shohl LLP

(57) ABSTRACT

The invention relates to measuring the concentration of analytes with the aid of an oxidase in an immersion sensor situated in a fluid or in a matrix containing fluid. Oxygen diffuses into the enzyme layer from within, from a gas-filled space connected to the atmosphere and/or to an oxygen reservoir. This enables oxygen saturation of the oxidase in a low-oxygen or oxygen-free medium and/or at high analyte concentrations. The analyte diffuses into the enzyme layer in a channel or a number of channels which contain(s) water and limit(s) diffusion, wherein the channel/channels on the surface of the sensor is/are filled with a protein-impermeable, hydrophilic matrix. By increasing the channel cross-section on the surface of the sensor and/or by connecting the channel/channels to a protein-impermeable, porous, hydrophilic layer on the surface of the sensor, the effect of outer deposits on the diffusion resistance of the analyte is reduced.

16 Claims, 1 Drawing Sheet

IMMERSION SENSOR FOR MEASURING THE CONCENTRATION OF AN ANALYTE WITH THE HELP OF AN OXIDASE

CROSS-REFERENCE TO RELATED APPLICATIONS

This application is a divisional application of and claims priority to U.S. application Ser. No. 10/687,529, filed Oct. 16, 2003, which is a continuation of PCT application PCT/CH02/00209, filed Apr. 15, 2002 which claims priority to German application number 10119036.0 filed Apr. 18, 2001, the contents of which are incorporated in their entirety by reference.

BACKGROUND

The present invention relates to measuring and testing. More particularly, the present invention relates to measuring the concentration of at least one analyte with the aid of an oxidase of an immersion sensor situated in a fluid or in a matrix containing fluid. The matrix is preferably an organic tissue, for example, a human or animal tissue. In preferred applications or uses of the present invention, the immersion sensor is implanted into the tissue. Subcutaneously implantable micro-sensors, on the basis of glucose oxidase as a preferred example of an oxidase, represent some particularly preferred exemplary applications for the diagnosis and intensive treatment of diabetes. Other preferred applications of the immersion sensor include measuring oxidase substrates in fluids with a low oxygen content.

Amperometric enzyme sensors for analyzing individual samples on the basis of analyte-specific oxidases can be regarded as technically mature. By contrast, immersion sensors on the basis of a oxidase reaction, which are inserted or implanted into a fluid or matrix containing analyte, are still in the process of technical development. If the concentration of dissolved oxygen is below the analyte concentration, the necessary oxygen saturation of the oxidase can only be achieved by selectively obstructing the diffusion of the analyte. The problem of oxygen saturation is accentuated in hypoxic media. Subcutaneously implantable amperometric microsensors, on the basis of glucose oxidase, have a potential area of application for the diagnosis and intensive treatment of diabetes mellitus [Bindra, D. D., Zhang, Y., Wilson, G., Sternberg, R., Thevenot, D. R., Moatti, D., Reach, G.: Anal Chem 63, 17, 1692-1696, 1991, DCCT Research Group, N Engl. J. Med. 329, 977-986, 1993, Fischer, U., Rebrin, K., v. Woedtke, T., Abel, P.: Horm. Metab. Res. 26, 515-522, 1994; Zick, R., Schiewitz, J.: Diabetes aktuell 4, 38-40, 2000]. Since the concentration of dissolved oxygen in the tissue is only a few hundredths of the glucose concentration, the layer containing enzyme is covered by a membrane whose permeability to oxygen is about a thousand times higher than its permeability to glucose. This is achieved by using permselective membranes [Schneider, H., Streicher S.: Artif Organs 9 (2), 180-183, 1985; Ward R S, W. K.: U.S. Pat. No. 5,428,123], so-called analyte windows, i.e. unselective pores or perforations in an oxygen-permeable, analyte-impermeable membrane [Abel, P., Kautek, W., v. Woedtke, T., Krüger, J.: DE 195 47 923.8 (1999)] or by using a sensor with different membranes on each side of the enzyme layer, wherein one membrane is permeable with a low permeability to the analyte and the other is only permeable to oxygen [Gough et al., Anal. Chem. 57, 2351-2357, 1985]. Implantable amperometric glucose sensors currently require recalibrating at certain time intervals, because the sensitivity is reduced over time. One of the possible causes for this is regarded as being an increase in the diffusion resistance of the glucose due to permeation-inhibiting deposits on the membrane or the analyte window [Rigby et al., Anal. Chim. Acta 385, 23-32, 1999, Thome-Duret, V., Gangerau, M. N., Zhang, Y., Wilson, G. S., Reach, G.: Diabetes Metab 22 (3), 174-178].

SUMMARY

It is an object of the invention to provide an immersion sensor and a method which ensure oxygen saturation of the oxidase of the immersion sensor at relatively low oxygen concentrations of a fluid or matrix or an adverse concentration ratio between the oxygen and the analyte. Preferably, the effect of any deposits on the diffusion resistance of the analyte is to be reduced.

The effect of any deposits on the diffusion resistance of the analyte is reduced in accordance with the invention by the fact that the analyte diffuses out of the matrix into the enzyme region, which is preferably an enzyme layer, in at least one channel containing water. The channel preferably forms the only way of transporting analyte to the enzyme. The diffusion resistance of the analyte is determined by the ratio of the length and the cross-section of the diffusion path. The length of the channel containing water is limited by the demands on the response time of the sensor, associated with the respective application. In some embodiments, the length of the channel is preferably 0.1 to 1 mm.

In one preferred embodiment, an increased effective cross-section of the diffusion channel or number of diffusion channels on the surface of the sensor leads to a leveling out of outer concentration gradients and so reduces the effect of outer deposits on the diffusion flow. The same effect is achieved in a second preferred embodiment by the channel or number of channels at or near the surface of the sensor passing into a hydrophilic, porous and protein-excluding layer bordering the matrix.

In one embodiment, the diffusion channel leads through a water-impermeable material and at the surface of the sensor is filled with a defined hydrophilic porous substance, e.g., regenerated cellulose, having a low molecular size exclusion limit and a high permeability to low-molecular substances. The exclusion limit of said substance prevents a change in the diffusion resistance due to the intrusion of proteins or other colloids. In one embodiment, for example, the channel is filled in with such a substance over its entire length.

The layer containing enzyme, i.e., containing oxidase, can for example be covered on the matrix side by a thin, analyte-impermeable, oxygen-permeable membrane having no analyte window, while the analyte diffuses from the matrix into the enzyme layer in at least one diffusion channel containing water. In the part limiting the flow, the length of the channel—or of each channel in the case of a number of channels—exceeds the thickness of the membrane, in some instances preferably by several fold.

If the oxygen content of the fluid or matrix to be examined is insufficient, or there is a wide concentration ratio between the analyte and the dissolved oxygen, oxygen saturation is achieved in accordance with the invention by the layer containing enzyme bordering an inner gas space of the sensor, for example a channel containing gas, from within. The gas phase in this channel is connected to an oxygen reservoir or to the atmosphere and enables the consumed oxygen to be replenished by diffusion or convection. The oxygen diffuses into the enzyme layer from within. In one embodiments, the diffusion path of the analyte, which causes the drop in concentration, preferably runs through membrane pores or diffusion channels to the enzyme layer from without. A thin oxygen-permeable membrane can be situated between the enzyme layer and the space containing gas. Alternatively, the enzyme layer containing water can directly border the gas phase of the channel. A convenient way of realizing the method in accordance with the invention and the immersion sensor in accordance with the invention is to bind the enzyme layer onto or into the swollen, porous, hydrophilic wall of a hollow fiber with a gas-filled lumen. Fluid can be prevented from intruding into the lumen of the hollow fiber by applying a slight pressure burden or by partially filling the lumen with finely dispersed hydrophobic fibers or particles. Due to their surface properties, the latter form wetting barriers to water or aqueous solutions. Since the gas-filled space communicates with the atmosphere or an oxygen reservoir, the oxygen consumed by the reaction between the oxidase and the analyte is replenished with little mass transfer resistance. In this way, high conversion rates, dependent on the analyte concentration, can be achieved irrespective of the oxygen content of the matrix.

Using a hollow fiber containing a gas enables ways of measuring enzyme conversion other than by applying the amperometric measuring principle. For barometrically detecting the oxygen consumption, the channel containing gas is connected to a pressure sensor. The small pressure measuring space thus provided can be periodically sealed off from the atmosphere by a micro-valve. The oxygen consumption then generates a decrease in the gas pressure, the rate of which depends on the concentration of the analyte. When the valve is closed, the oxygen partial pressure in the pressure measuring space drops to a near-zero value, and the analyte consumption is then significantly retarded. By opening the micro-valve before the next measuring cycle, the pressure measuring space is again enriched with oxygen. Continuous barometric detection can be achieved by introducing a gas diffusion resistance, adjusted to the reaction rate, between the pressure measuring space and the atmosphere. If the lumen of the pressure measuring space is connected to the atmosphere by one or more fine pores or capillaries, the pressure difference with respect to the atmosphere is proportional to the analyte conversion in the steady state. If the lumen of the pressure measuring space is sufficiently small, the decrease in pressure reacts, with a lower transition time, to changes in the analyte conversion.

There are in principle other ways of measuring the conversion of oxidase in an immersed or implanted sensor, for example by detecting the oxygen concentration in an external gas analysis space. In order to ensure a continuous flow of gas through the channel containing gas in the immersion sensor and the subsequent outer gas analysis space, micro-dialysis probes comprising oxidase immobilized in the hollow fiber membrane can be used. Due to the low convection resistance of slowly flowing gases, very narrow capillaries can be used and the gas analysis space can be arranged at a certain distance from the actual immersion sensor or implantable sensor. Electrochemical or optical measuring devices can be used to analyze the gas conversion, e.g., the decrease in the oxygen content or the formation of volatile reaction products such as hydrogen peroxide.

DETAILED DESCRIPTION

Figure 1:
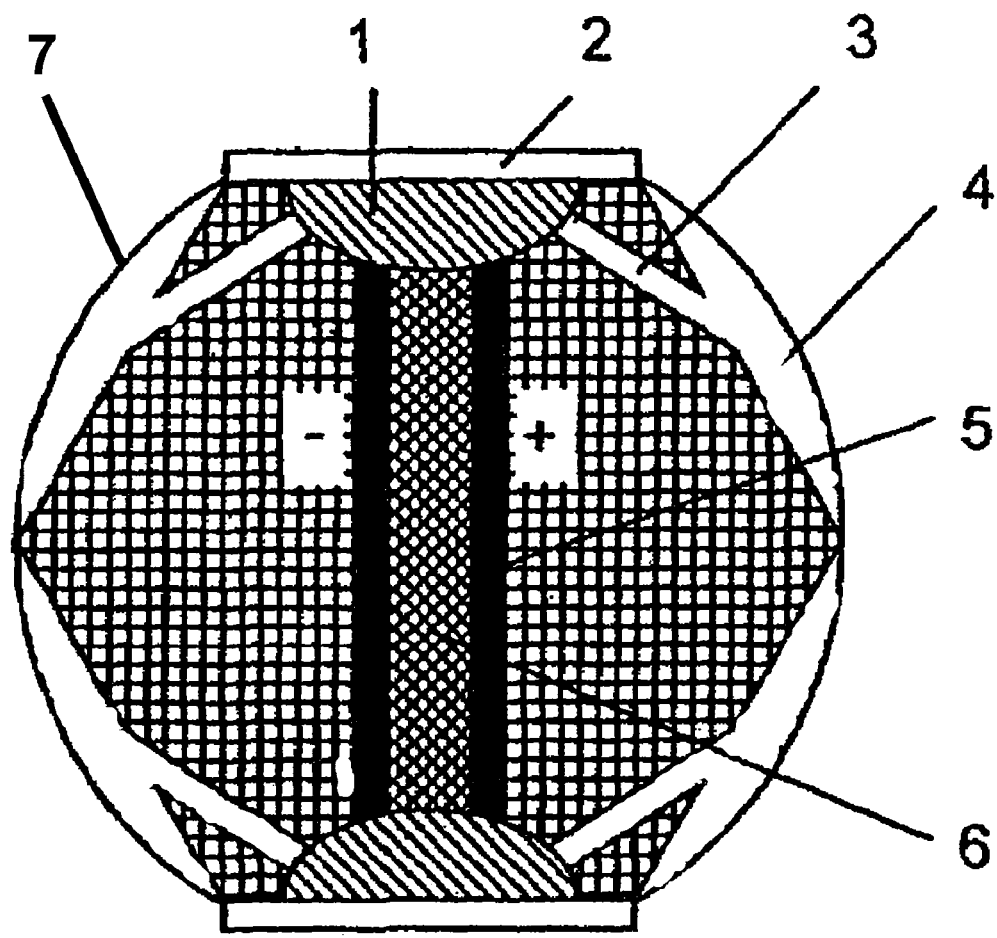
FIG. 1 depicts one embodiment of an immersion sensor according to the present invention.

In this description, the invention is explained by way of exemplary embodiments. Features and steps disclosed by the exemplary embodiments, and suitable alternative or equivalents, each individually and in any combination, i.e., a combination of one or more features and/or steps, are intended to be encompassed in the present invention.

EXAMPLE 1

A solution of glucose oxidase and catalase (each 0.3%), serum albumin (2%) and sodium alginate (2%) in an ammonium hydrogen carbonate solution (pH 7.8) is absorbed through 20 cm long segments of a hollow fiber made of regenerated cellulose (G-O-P GmbH, Pirna, Germany) having an inner diameter of 190 µm and an outer diameter of about 210 µm. The enzyme layer adhering to the inner side of the lumen is then cross-linked in an atmosphere saturated with water vapor and glutaraldehyde. The hollow fiber is washed in water containing glycine and later in water containing glycerol and dried in the coldness of the air. The hollow fiber is then divided up into 1.5 cm long segments. For manufacturing a sensor, such a segment is inserted into special 1.8 cm long high-grade steel cannulae of appropriate diameter, for example having an inner diameter of approx. 0.25 mm and an outer diameter of approx. 0.35 mm. In their roughly 1.3 cm long apical section, the cannulae have pores which are calculated in their size and spacing such that a defined diffusion resistance of glucose (glucose concentration/glucose consumption) in the range of 50 to 100 s µl$^{-1}$ is achieved. If the enzyme reaction is limited by this resistance, then for a concentration of 5 nmol l$^{-1}$, a glucose consumption of 3 to 6 nmol/min results, which in the case of amperometric detection would generate a reaction current in the microampere range. The glucose consumption thus set, which roughly corresponds to the glucose withdrawal in the case of microdialysis at a flow rate of 5 µl per hour, does not yet cause a reduction in the glucose concentration in the vicinity of the hollow fiber. At the tip of the cannula and at the base up to the slits, the hollow fiber is fastened sealed with self-hardening polyacrylate adhesive and the lumen is sealed at the tip; at the base, it remains open. In order to prevent fluid from intruding into the lumen of the hollow fiber, the lumen of the hollow fiber is filled with fine hydrophobic fibers. The cannula is connected via the open base to the measuring space of a micro-pressure sensor (measuring range 200 mbar). The measuring space of the pressure sensor has a volume of approx. 1 µl, the gas-filled lumen of the hollow fiber a volume of approx. 0.5 µl. The measuring space of the pressure sensor and the atmosphere are connected by a fine cannula or a fine channel filled with porous material, which generate a gas diffusion resistance (oxygen concentration/oxygen consumption) of approx. 20 s µl$^{-1}$. If the sensor is introduced into a solution containing glucose, with glucose concentrations of 1 to 30 mM, the outer glucose diffusion resistance limits the concentration-dependent glucose consumption to 0.6 to 36 nmol min$^{-1}$ or the oxygen consumption to 15 to 600 nl min$^{-1}$. The gas diffusion resistance causes a drop in the oxygen concentration and a corresponding drop in pressure with respect to the atmosphere. At a glucose concentration of 5 mM or an oxygen consumption of about 100 nl min$^{-1}$, this decrease in pressure is 20 to 30 mbar and can therefore be detected exactly. Since the oxygen content of the measuring space is very low (approx. 10 nmol), changes in the conversion rate are registered with a delay of less than 3 min. The sensitivity of the sensor can be increased by connecting the pressure sensor and the measuring space, via the gas diffusion resistance, to an oxygen reservoir of preferably about 10 to 20 ml which is filled with pure oxygen. A slight pressure burden in this oxygen reservoir of preferably approx. 300 mbar with respect to atmospheric pressure prevents water from intruding into the lumen of the hollow fiber, making it unnecessary to insert fibers or particles.

EXAMPLE 2

An immersion sensor according to a second exemplary embodiment is shown in FIG. 1.

The base body 7 of the sensor is rod-shaped and consists of insulating plastic comprising high-grade steel electrodes 5 lying in parallel and terminating in two recesses lying on opposite sides of the body 7 and containing enzyme layers 1. A space 6 between the electrodes 5 and the enzyme layers 1 can be designed to contain gas and conduct gas, by being filled with a porous, hydrophobic material, e.g. polypropylene foam, or by being filled in by the plastic material of the base body 7. The enzyme layers 1 are each covered by a thin membrane 2 which is impermeable to the analyte and to salts. If the space 6 between the enzyme layers is filled with plastic, the surface membrane 2 is permeable to oxygen. Narrow diffusion channels 3 containing water lead laterally and with a defined spacing from the enzyme layer 1 to the surface of the sensor. They terminate in a porous layer 4 lying outside the membrane region 1, 2 and made of regenerated cellulose having a molecular size exclusion limit for proteins in the range of 5 to 10 kDa.

In the case of membrane-controlled oxygen diffusion, the ratio (Q) of the diffusion resistances to the analyte ($R_a$) and the oxygen ($R_o$) follows from a geometrical factor (G) and the ratio between the diffusion coefficient of the oxygen in the membrane ($D_o$) and the diffusion coefficient of the analyte in the diffusion channels ($D_a$). $D_a$ differs little from the diffusion coefficient of the analyte in water.

$$Q = R_a/R_o = G \times D_o/D_a.$$

The geometrical factor (G) is calculated from the area ($A_m$) and the thickness ($d_m$) of the oxygen-permeable membrane 2 and the sum of the length ($d_k$) and the sum of the cross-sectional areas ($A_k$) of the diffusion channels 3 for the analyte.

$$G = \frac{A_m \cdot d_k}{A_k \cdot d_m}$$

A number of degrees of freedom result in order to adjust the ratio (Q) to the task of measuring. For some particular examples: the number of channels 3; the lengths and cross-sections of the channels 3; the thickness of the oxygen-permeable membrane 2; and the diffusion coefficient of the material of the membrane to oxygen. It should be taken into account that for a cannula length of more than 0.3 mm, the time requirement for setting the analyte diffusion steady state becomes a matter of minutes, and for a cannula length of 0.5 mm is already 4 to 5 minutes. This time requirement (t) may be calculated, according to Crank in "The mathematics of diffusion", Clarendon Press, Oxford, 1956, from the diffusion coefficient (D) for glucose and the length of the diffusion path L, with the aid of the equation:

$$t = \frac{1}{6} \ast L^2.$$

Since the cross-sectional area of the channel is small compared to the area of the outer layer of regenerated cellulose, the concentration gradient of the analyte outside the surface of the sensor levels off sharply, and the entire diffusion resistance becomes insensitive to material deposits on the surface of the sensor.

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

In the figure, the reference numerals designate:
1: an enzyme layer;
2: an analyte-impermeable and oxygen-permeable membrane (may be oxygen-permeable as applicable);
3: a diffusion channel for the analyte;
4: a near-surface part of the diffusion channel for the analyte;
5: electrodes;
6: a part of the sensor in which a channel containing gas may be located.

The invention claimed is:

1. A method for measuring the concentration of at least one analyte with the aid of an analyte-specific oxidase, said method comprising:
   providing an immersion sensor, said immersion sensor comprising at least one enzyme region with the analyte-specific oxidase immobilized therein, two electrodes lying in parallel and terminating in the at least one enzyme region, at least one space for gaseous oxygen formed in between and bordering the electrodes and bordering the at least one enzyme region directly or via an oxygen-permeable material, and at least one channel leading from the at least one enzyme region to a surface of the immersion sensor which limits diffusion and contains water;
   introducing said at least one analyte into said immersion sensor, wherein said at least one analyte diffuses into said at least one enzyme region via said at least one channel and wherein said at least one analyte reacts with said analyte-specific oxidase, consuming oxygen and producing volatile hydrogen peroxide;
   measuring the concentration of the at least one analyte by measuring amperometrically the reaction of the at least one analyte with said analyte-specific oxidase with the immersion sensor; and
   correlating the concentration of the at least one analyte with said hydrogen peroxide production.

2. The method as set forth in claim 1, wherein introducing said at least one analyte into said immersion sensor comprises the at least one analyte flowing out of a surrounding matrix into the at least one channel over an increased effective area as compared to the cross-section of a contact area with the at least one enzyme region and the at least one channel.

3. The method as set forth in claim 1, wherein the at least one channel is filled, at the surface of said immersion sensor or completely, with a hydrophilic substance having a permeability to the at least one analyte.

4. The method of claim 3, wherein the hydrophilic substance has a molecular size exclusion limit in the range of about 5 kDa to about 10 kDa.

5. The method as set forth in claim 1, wherein the oxygen needed for oxidizing the at least one analyte diffuses from within, directly from said at least one space for gaseous oxygen or via an oxygen-permeable membrane, into the at least one enzyme region.

6. The method as set forth in claim 5, wherein oxygen from the atmosphere or from an oxygen reservoir is guided into said at least one space for gaseous oxygen.

7. The method as set forth in claim 1, wherein the at least one enzyme region contains water.

8. The method as set forth in claim 7, wherein said at least one space for gaseous oxygen is connected to one of the atmosphere or a gas reservoir containing oxygen.

9. The method as set forth in claim 7, wherein said at least one space for gaseous oxygen includes hydrophobic solid surfaces which generate a wetting barrier for aqueous solutions and water.

10. The method as set forth in claim 9, wherein said at least one space for gaseous oxygen is filled in by a porous film made of polypropylene.

11. The method as set forth in claim 1, wherein the at least one enzyme region is an enzyme layer.

12. The method as set forth in claim 11, wherein the portion of the surface of the enzyme layer not bordering the electrodes, the at least one space for gaseous oxygen, and the at least one channel, is covered by an analyte-impermeable, oxygen-permeable membrane which separates said portion of the surface of the enzyme layer from the exterior of the immersion sensor.

13. The method as set forth in claim 12, wherein, other than the analyte-impermeable, oxygen-permeable membrane bordering the enzyme layer, the surface of the immersion sensor comprises at least one porous layer.

14. A method for measuring the concentration of at least one analyte with the aid of an analyte-specific enzyme, said method comprising:
    providing an immersion sensor, said immersion sensor comprising at least one enzyme region with the analyte-specific enzyme therein, two electrodes lying in parallel and terminating in the at least one enzyme region, at least one space for gaseous oxygen formed in between and bordering the electrodes and bordering the at least one enzyme region directly or via an oxygen-permeable material, and at least one channel leading from the at least one enzyme region to a surface of the immersion sensor which limits diffusion and contains water;
    introducing said at least one analyte into said immersion sensor, wherein said at least one analyte diffuses into said at least one enzyme region via said at least one channel, and wherein said at least one analyte reacts with said analyte-specific enzyme, consuming oxygen;
    measuring the concentration of the at least one analyte by measuring amperometrically the reaction of the at least one analyte with said analyte-specific enzyme with the immersion sensor; and
    correlating the concentration of the at least one analyte with said oxygen consumption.

15. The method according to claim 14, wherein the at least one channel contains water.

16. The method according to claim 14, wherein the analyte-specific enzyme is an oxidase.

* * * * *